US007638471B2

(12) United States Patent
Moaddel et al.

(10) Patent No.: US 7,638,471 B2

(45) Date of Patent: Dec. 29, 2009

(54) TRANSPARENT CLEANSING BAR COMPRISING FLIPPED N-ACYL GLUTAMATE

(75) Inventors: Teanoosh Moaddel, Watertown, CT (US); Yury Yarovoy, Monroe, CT (US)

(73) Assignee: Conopco, Inc.,, Englewood Cliffs, NJ (US)

( * ) Notice: Subject to any disclaimer, the term of this patent is extended or adjusted under 35 U.S.C. 154(b) by 40 days.

(21) Appl. No.: 11/951,523

(22) Filed: Dec. 6, 2007

(65) Prior Publication Data

US 2009/0149370 A1 Jun. 11, 2009

(51) Int. Cl.
*A61K 7/00* (2006.01)

(52) U.S. Cl. ....................... 510/141; 510/147; 510/152; 510/155; 510/499

(58) Field of Classification Search ....................... None
See application file for complete search history.

(56) References Cited

U.S. PATENT DOCUMENTS

| | | | |
|---|---|---|---|
| 3,663,459 | A | 5/1972 | Yoshida et al. |
| 4,273,684 | A | 6/1981 | Nagashima et al. |
| 5,098,608 | A | 3/1992 | Miyazawa et al. |
| 5,518,665 | A | 5/1996 | Kaneko et al. |

FOREIGN PATENT DOCUMENTS

| | | | |
|---|---|---|---|
| DE | 100 29 932 | A1 | 12/2001 |
| EP | 0 426 984 | A2 | 5/1991 |
| JP | 8291123 | | 8/1996 |

OTHER PUBLICATIONS

Written Opinion of the International Searching Authority mailed Apr. 21, 2009.
International Search Report mailed Apr. 21, 2009.

*Primary Examiner*—Necholus Ogden, Jr.
(74) *Attorney, Agent, or Firm*—Ronald A. Koatz

(57) ABSTRACT

The invention provides transparent, pH neutral solid bar compositions comprising flipped N-acyl glutamate surfactants.

7 Claims, 1 Drawing Sheet

(a)

(a)

TRANSPARENT CLEANSING BAR COMPRISING FLIPPED N-ACYL GLUTAMATE

FIELD OF THE INVENTION

The present invention relates to transparent (e.g., optically clear) cleansing bars comprising "flipped N-acyl glutamate" surfactants (as defined below). In preferred embodiments a 10% solution of such bar has a pH in the range of 5 to 8.

BACKGROUND

Bars which have a pH of between 5 and 8 and which are optically transparent (e.g., optically clear in that light is transmitted so that a body lying on the opposite side is entirely visible) are highly desirable.

Bars have previously been made using fatty acyl amino acid surfactants, for example, alkyl glutamates. Alkyl glutamates have a structure as follows:

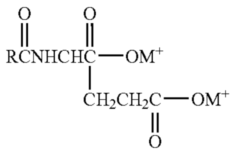

wherein R is straight or alkenyl group having 6 to 24 carbons; and M is an alkali or alkaline metal, typically sodium or potassium, or trialkanolamine.

As noted, a number of references disclose use of such fatty acylamino acids in bars. U.S. Pat. No. 3,663,459 to Yoshida et al., for example, relates to detergent bars comprising water soluble salts of N-acyl-glutamic acids and N-acyl aspartic acids. The bars are opaque in appearance. U.S. Pat. No. 4,273,684 to Nagashima et al. discloses transparent bars containing basic amino acid salt of N-long chain acyl optically active acidic amino acid. U.S. Pat. No. 5,098,608 to Miyazawa discloses transparent solid detergent compositions containing N-acyl acidic amino acid salts.

JP 8291123 to Lion Corp. discloses certain types of surfactant structures similar to those of the subject invention. There is no disclosure of the compounds, however, in bar compositions and it is unpredictable that use of such compounds in bars would lead to optical transparency.

It would be greatly desirable to find molecules, other than those currently used, which could be used in bar compositions to provide a combination of optical transparency and pH neutrality (i.e., pH 5 to 8). Unexpectedly, applicants have found specific molecules which obtain these objectives.

BRIEF DESCRIPTION OF INVENTION

The present invention relates to transparent, pH-neutral (and consequently mild), solid bar compositions comprising "flipped" N-acyl-glutamate surfactant molecules as follows:

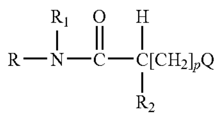

wherein

R is an alkyl or alkenyl group having 8 to 20 carbons, preferably 12 to 18 carbons;

$R_1$ is preferably hydrogen, but may be short chain $C_nH_{2n+1}$ group, where n=1 to 3 (e.g., methyl, ethyl);

$R_2$ may be hydrogen, short chain $C_nH_{2n+1}$ group such as methyl, ethyl and which optionally has surfactant head group such as COOH, $SO_3$ or $PO_4$ (e.g., $CH_2CH_2COOH$);

p is 0-2; and

Q is a functional group such as COOH, $SO_3$ or $PO_4$ (with counterion forming the surfactant).

The chemical structure of the above-noted 4 (carboxyalkyl)-monoglutaramides can be viewed as similar to that of N-acyl-glutamates with the main distinction that carbonyl (—C═O) and amino (—NH) groups are exchanged or "flipped". Thus, 4 (carboxyalkyl)-monoglutaramides can be referred to as carbonyl-amine (CO/NH) flipped N-acyl-glutamates or simply "flipped" N-acyl-glutamates. We will use this terminology hence forward in the description of the invention. Other flipped N-acyl amino acids derivatives may be also used in the combination with flipped N-acyl-glutamate. The examples include, but are not limited to N-acyl-malonamides (or flipped N-acyl-glycinates), flipped N-acyl sarcosinates, etc.

More specifically, the invention relates to solid bar compositions comprising flipped N-acyl glutamate. In preferred embodiments of the invention, it is desirable to form trialkanolamine (e.g., triethanolamine) salts of the flipped N-acyl glutamic acid. This can be done by mixing flipped N-acyl glutamic acid, trialkanolamine and water, followed by extrusion. Mixing was done on a small scale by adding the flipped N-acyl glutamic acid, trialkanolamine and water to small scale mixer (DACA mixer, for example). Material was mixed at about 40 to 50° C., preferably at 45° C., at about 100 rpm for about 30-60 minutes and then extruded. The extruded noodles were transparent.

In one embodiment of the invention, as noted, bars are made by mixing flipped N-acyl glutamic acid, trialkanolamine (or other base, e.g., alkali metal hydroxide) and water under conditions noted above, followed by extrusion. The flipped N-acyl glutamic acid, water, and trialkanolamine (and/or other base) can be optionally mixed with co-surfactant, polyols, polymers and other ingredients typically included in bar compositions.

In a second embodiment, the bars can be prepared via a cast-melt process using flipped N-acyl glutamate (neutralized flipped glutamic acid) and appropriate solvent. Compositions made via cast melt typically comprise the flipped surfactant and trialkanolamine, water and for example ethanol. Typically, the solvent system is used to allow formation of isotropic liquid above 60° C., the composition is poured into open molds and the composition solidifies after cooling and evaporation of volatiles (e.g., alcohol solvent).

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
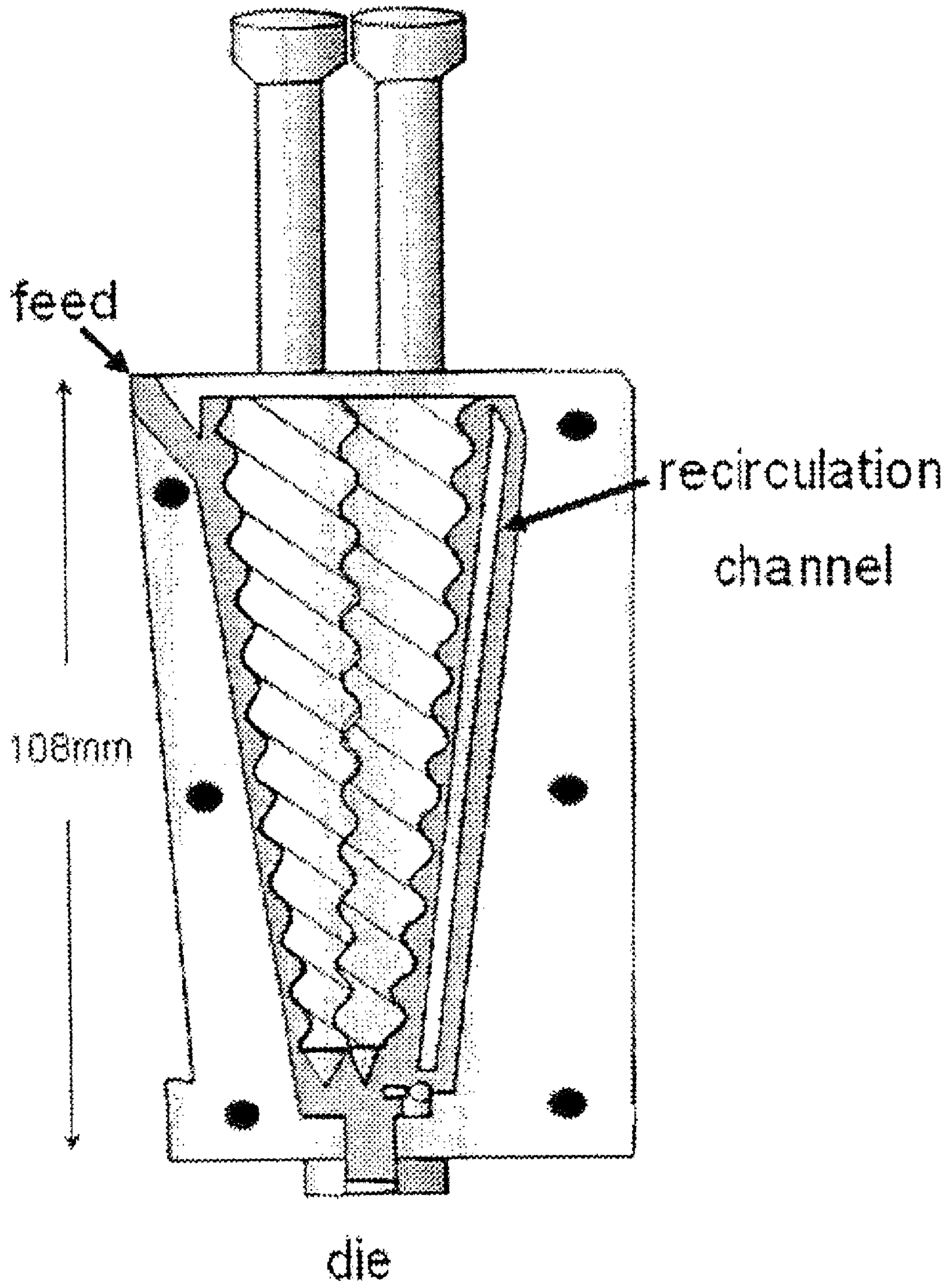
FIG. 1 is a schematic of the type of small scale mixer (e.g., DACA mixer) used when mixing, e.g., flipped glutamic acid, trialkanolamine and water according to process to make bars of the invention.

The present invention relates to transparent, pH-neutral solid bar compositions. The compositions comprise alkali metal and/or trialkanolamine salts of flipped N-acyl glutamic acid (as defined) having the following structure:

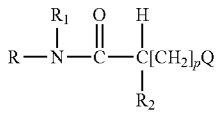

wherein

R is an alkyl or alkenyl group having 8 to 20 carbons, preferably 12 to 18 carbons;

$R_1$ is preferably hydrogen, but may be short chain $C_nH_{2n+1}$ group, where n=1 to 3 (e.g., methyl, ethyl);

$R_2$ may be hydrogen short chain $C_nH_{2n+1}$ group such as methyl, ethyl and which optionally has surfactant head group such as COOH, $SO_3$ or $PO_4$ (e.g., $CH_2CH_2COOH$);

p is 0-2; and

Q is functional group such as COOH, $SO_3$ or $PO_4$ (with counterion forming the surfactant).

In a preferred embodiment, molecules are salts of the structure above wherein p=0, Q=COOH and $R_2$ is $CH_2CH_2COOH$.

By pH neutral is meant that the pH of a 10% aqueous solution of the bar is in the range of about 5 to 8, preferably 6 to 8, more preferably about 6.5 to 7.5.

By transparent is meant that, when light is transmitted through the bar, there is no appreciable scattering such that an object or body on the opposite side is entirely visible to the eye.

More specifically, compositions of the invention may comprise:

(a) 30 to 80%, preferably 40 to 75% by wt., flipped N-acyl glutamate (bar may have up to about 10% non-neutralized flipped N-acyl glutamic acid)

(b) 0 to 15% by wt. co-surfactant selected from the group consisting of anionic, nonionic, zwitterionic/amphoteric and cationic surfactant and mixtures thereof;

(c) optionally from 0% up to about 7% excess trialkanolamine; and (d) 0 to 65%, preferably 1 to 60%, more preferably 10 to 55% by wt. water.

Typically the bar is obtained by mixing trialkanolamine (and/or other base) and flipped fatty acyl glutamic acid together with water such that the final amount of water is in the range of 0 to 65%, preferably 1 to 60% by wt. water. This mixture can then be extruded.

In another embodiment of the invention, the bars of the invention can be formed by a cast-melt process. In such process, the compositions formed will be mixed with solvents (e.g., ethanol and/or other polyols). Ingredients are heated to about 80° C. until a transparent liquid is produced and then poured into molds where they are cooled and allowed to dry so that the volatile components can evaporate to form hard bars.

Typically compositions will have about 30 to 80%, preferably 40 to 75% of the flipped N-acyl glutamate (bar may have up to about 10% non-neutralized flipped glutamic acid); 0 to 7% excess trialkanolamine; 0 to 65%, preferably 1 to 60%, more preferably 10 to 55% water; and 5 to 25% alkanol (e.g., ethanol, isopropylalcohol) and/or other polyols (e.g., glycerine). The compositions may further comprise 0 to 15% co-surfactant.

The compositions are described in further detail below.

As noted, the first required component of the bars of the invention are the flipped N-acyl glutamate molecules as defined above. These are formed by mixing flipped fatty acyl glutamic acid, trialkanolamine and/or other base (e.g., alkali metal hydroxide) and water using, for example, the mixer.

In addition to the flipped fatty acyl glutamate, compositions of the invention may comprise 0 to 15% by wt. co-surfactant selected from the group consisting of anionic, nonionic, zwitterionic/amphoteric and cationic surfactant, and mixtures thereof.

Suitable anionic detergent active compounds are water soluble salts of organic sulphuric reaction products having in the molecular structure an alkyl radical containing from 8 to 22 carbon atoms, and a radical chosen from sulphonic acid or sulphuric acid ester radicals, and mixtures thereof.

Examples of suitable anionic detergents are sodium and potassium alcohol sulphates, especially those obtained by sulphating the higher alcohols produced by reducing the glycerides of tallow or coconut oil; sodium and potassium alkyl benzene sulphonates such as those in which the alkyl group contains from 9 to 15 carbon atoms; sodium alkyl glyceryl ether sulphates, especially those ethers of the higher alcohols derived from tallow and coconut oil; sodium coconut oil fatty acid monoglyceride sulphates; sodium and potassium salts of sulphuric acid esters of the reaction product of one mole of a higher fatty alcohol and from 1 to 6 moles of ethylene oxide; sodium and potassium salts of alkyl phenol ethylene oxide ether sulphate with from 1 to 8 units of ethylene oxide molecule and in which the alkyl radicals contain from 4 to 14 carbon atoms; the reaction product of fatty acids esterified with isethionic acid and neutralized with sodium hydroxide where, for example, the fatty acids are derived from coconut oil and mixtures thereof.

The preferred water-soluble synthetic anionic detergent active compounds are the alkali metal (such as sodium and potassium) and alkaline earth metal (such as calcium and magnesium) salts of higher alkyl benzene sulphonates and mixtures with olefin sulphonates and higher alkyl sulphates, and the higher fatty acid monoglyceride sulphates.

Suitable nonionic detergent active compounds can be broadly described as compounds produced by the condensation of alkylene oxide groups, which are hydrophilic in nature, with an organic hydrophobic compound which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

Particular examples include the condensation product of aliphatic alcohols having from 8 to 22 carbon atoms in either straight or branched chain configuration with ethylene oxide, such as a coconut oil ethylene oxide condensate having from 2 to 15 moles of ethylene oxide per mole of coconut alcohol; condensates of alkylphenols whose alkyl group contains from 6 to 12 carbon atoms with 5 to 25 moles of ethylene oxide per mole of alkylphenol; condensates of the reaction product of ethylenediamine and propylene oxide with ethylene oxide, the condensate containing from 40 to 80% of polyoxyethylene radicals by weight and having a molecular weight of from 5,000 to 11,000; tertiary amine oxides of structure $R_3NO$, where one group R is an alkyl group of 8 to 18 carbon atoms and the others are each methyl, ethyl or hydroxyethyl groups, for instance dimethyldodecylamine oxide; tertiary phosphine oxides of structure $R_3PO$, where one group R is an alkyl group of from 10 to 18 carbon atoms, and the others are each alkyl or hydroxyalkyl groups of 1 to 3 carbon atoms, for instance dimethyldodecylphosphine oxide; and dialkyl sulphoxides of structure $R_2SO$ where the group R is an alkyl group of from 10 to 18 carbon atoms and the other is methyl or ethyl, for instance methyltetradecyl sulphoxide; fatty acid alkylolamides; alkylene oxide condensates of fatty acid alkylolamides and alkyl mercaptans.

It is also possible to include cationic, amphoteric, or zwitterionic detergent actives in the compositions according to the invention Suitable cationic detergent actives that can be incorporated are alkyl substituted quarternary ammonium halide salts e.g. bis(hydrogenated tallow) dimethylammonium chlorides, cetyltrimethyl ammonium bromide, benzalkonium chlorides and dodecylmethylpolyoxyethylene ammonium chloride and amine and imidazoline salts for e.g. primary, secondary and tertiary amine hydrochlorides and imidazoline hydrochlorides.

Suitable amphoteric detergent-active compounds that optionally can be employed are derivatives of aliphatic secondary and tertiary amines containing an alkyl group of 8 to 18 carbon atoms and an aliphatic radical substituted by an anionic water-solubilizing group, for instance sodium 3-dodecylamino-propionate, sodium 3-dodecylaminopropane sulphonate and sodium N-2-hydroxydodecyl-N-methyltaurate.

Suitable zwitterionic detergent-active compounds that optionally can be employed are derivatives of aliphatic quaternary ammonium, sulphonium and phosphonium compounds having an aliphatic radical of from 8 to 18 carbon atoms and an aliphatic radical substituted by an anionic water-solubilizing group, for instance 3-(N—N-dimethyl-N-hexadecylammonium) propane-1-sulphonate betaine, 3-(dodecylmethyl sulphonium) propane-1-sulphonate betaine and 3-(cetylmethylphosphonium) ethane sulphonate betaine.

Benefit agents may comprise up to 30% by weight of the composition. The benefit agents are generally skin benefit materials such as moisturizers, emollients, sunscreens, or anti-aging compounds, and are incorporated at any step prior to step of milling. Alternatively certain of these benefit agents may be introduced as macro domains during plodding.

Examples of moisturizers and humectants include polyols, glycerol, cetyl alcohol, carbopol 934, ethoxylated castor oil, paraffin oils, lanolin and its derivatives. Silicone compounds such as silicone surfactants like DC3225C (Dow Corning) and/or silicone emollients, silicone oil (DC-200 Ex-Dow Corning) may also be included. Sun-screens such as 4-tertiary butyl-4'-methoxy dibenzoylmethane (available under the trade name PARSOL 1789 from Givaudan) and/or 2-ethyl hexyl methoxy cinnamate (available under the trade name PARSOL MCX from Givaudan) or other UV-A and UV-B sun-screens may also be used.

Structurants which may be used to structure the bar include fatty acid soap, polyalkylene glycol or even sugar structurants (maltodextrin or starch). These may comprise 0 to 10% by wt. of the final composition.

Polyols and inorganic electrolytes may be used to harden bars. Polyols are defined as molecules with multiple hydroxyl groups and include glycerol, propylene glycol, sorbitol and polyvinyl alcohol.

Inorganic electrolytes include monovalent chloride salts like sodium chloride; monovalent and divalent sulphate salts (sodium sulfate, sodium carbonate); aluminate salts; monovalent phosphates, phosphonates; and mixtures thereof.

Another class of hardening agent, includes insoluble inorganic or mineral solids that can structure. These include silica (fumed, precipitated or modified), alumina, calcium carbonate, kaolin and talc.

In addition, optional ingredients include chelating agents such as EDTA; preservatives (Glydant®), antioxidants, natural and synthetic perfumes and skin benefit agents such as noted above.

Bars may also include sensory modifiers and enhancers of desirable end use properties. These include coloring agents, opacifiers and pearlizers (zinc stearate, $TiO_2$), ethylene glycol monostearate, and styrene/acrylate copolymers. They may further comprise mono or diethanolamide amides as suds boosters.

Cationic polymers as conditioners which may be used include polyquaternium, Merquat® polymers, and Jaguar® polymers. Polyethylene glycols may be used as conditioners as well (e.g., Polyox® polymers).

Bars of the invention also comprise 0 to 65%, preferably 1 to 60% by wt. water, more preferably 10 to 55% by wt. water.

Typically, the pH of bars of the invention is about 5 to 8, preferably about 6 to 8.

EXAMPLES

Example 1

Inventive

A DACA mixer was used to mix components as follows:

(1) 38% flipped N-acyl glutamic acid;

(2) 28.7% triethanolamine; and (3) 33.3% water.

After mixing, we obtained composition comprising approximately:

(1) 62% flipped N-acyl glutamate;

(2) 5% unreacted flipped N-acyl glutamic acid; and (3) 33% water.

General specification for mixing are given in Table 1 below:

TABLE 1

| Micro-compounder (Daca) | | |
|---|---|---|
| Specification | | units |
| Barrel temperature (max.) | 400 | |

TABLE 1-continued

| Micro-compounder (Daca) | | |
|---|---|---|
| Specification | | units |
| Torque (max.) | 6.2 | N · m |
| Motor speed (max.) | 360 | Rpm |
| Mixing volume | 5 | $cm^3$ |
| Dimensions | 30.48w × 53.34d × 68.58h | Cm |

It should be noted that the Daca Instrument unit used is no longer manufactured. However, the vertical micro compounder is now available at DSM Xplore (see www.xplore-together.com). A schematic of Daca mixer is shown in FIG. 1.

Example 2

Inventive

A DACA mixer was used to mix components as follows:

(1) 25% flipped N-acyl glutamic acid;

(2) 25% triethanolamine; and (3) 50% water.

After mixing, we obtained a composition comprising approximately:

(1) 47% flipped N-acyl glutamate;

(2) 3% triethanolamine; and (3) 50% water.

Example 3

Inventive

By cast melt followed by evaporation

The following were mixed at 80° C. until a clear liquid was formed:

(1) 34.2% flipped N-acyl glutamic acid;

(2) 25.8% triethanolamine;

(3) 30% water; and (4) 10% ethanol.

The resulting liquid was then poured into a mold to form a transparent bar having the following composition:

(1) 55% flipped N-acyl glutamate;

(2) 5% flipped N-acyl glutamic acid;

(3) 30% water; and (4) 10% ethanol.

Example 4

Inventive

By cast melt w/o evaporation provided that samples are kept in closed container.

The following were mixed at 80° C. until a clear liquid was formed:

(1) 41.1% flipped N-acyl glutamic acid;

(2) 19.3% aqueous NaOH (50/50 w/w); and (3) 39.6% water.

The resulting liquid was then poured into a mold to form a transparent bar having the following composition:

(1) 46% flipped N-acyl glutamate; and (2) 54% water.

Example 5

Inventive

By cast melt w/o evaporation provided that kept in closed container.

The following were mixed at 80° C. until a clear liquid was formed:

(1) 37.38 flipped N-acyl glutamic acid;

(2) 33.25% aqueous KOH (50 w/v); and (3) 29.37% water.

The resulting liquid was then poured into a mold to form a transparent bar having the following composition:

(1) 45% flipped N-acyl glutamate;

(2) 55% water.

For Examples 1 to 2 (extrusion), each of the components were added in amounts indicated to a small scale DACA mixer as describe in Example 1. The materials were mixed at about 40 to 50° C., preferably 45° C. at about 100 rpm for about 30-60 minutes. The material was extruded to noodles. The noodles may be optionally stamped into bars.

For Examples 3 (cast melt), the compounds were mixed and heated to a temperature of about 80° C. until the components formed a transparent liquid (i.e., liquid transparent to naked eye) at these temperatures. The mixture was then poured into open molds and volatiles (i.e., alcohol) allowed to evaporate.

For examples 4 and 5 (cast melt without evaporation) the compounds were mixed at a temperature of about 80° C. to form a transparent liquid. The mixture was then poured into closed molds and allowed to cool.

The invention claimed is:

1. A transparent bar composition comprising flipped N-acyl glutamate surfactant having the following structure:

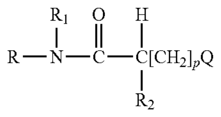

wherein

R is an alkyl or alkenyl group having 8 to 20 carbons;

$R_1$ is hydrogen, or short chain $C_nH_{2n+1}$ group, where n=1 to 3;

$R_2$ is hydrogen, short chain $C_nH_{2n+1}$ group comprising a surfactant head group;

p is 0-2; and

Q is functional group.

2. A bar composition according to claim 1 wherein $R_1$ is hydrogen, p=0 Q=COOH, $SO_3$ or $PO_4$ and $R_2$ is $CH_2CH_2COOH$.

3. A bar composition comprising:

(a) 30 to 80% by wt. flipped N-acyl glutamate of claim 1;

(b) 0 to 15% by wt. co-surfactant selected from the group consisting of anionic, nonionic, zwitterionic/amphoteric and cationic surfactant and mixtures thereof;

(c) from 0% to about 7% by wt. excess trialkanolamine;

(d) 0 to 65% by wt. water.

wherein the bar may optionally comprise up to 10% by wt. flipped N-acyl glutamic acid.

4. A process for making composition of claim 3 comprising:

(a) mixing components (a); (b); trialkanolamine and/or alkali metal base; and water at 100 rpm in a mixer at temperature of about 40 to 50° C., (b) extruding to format transparent noodle; and optionally stamping noodles into a bar.

5. A bar composition comprising (a) 30 to 80% by wt. flipped N-acyl glutamate;

(b) 0 to 15% by wt. co-surfactant selected from the group consisting of anionic, nonionic, zwitterionic/amphoteric and cationic surfactants and mixtures thereof;

(c) 0% to about 7% by wt. excess trialkanolamine;

(e) 5 to 25% by wt. alcohol solvent; and (f) 0 to 65% by wt. water;

wherein the bar may optionally comprise up to 10% by wt. flipped N-acyl glutamic acid.

6. A melt cast process for making compositions of claim 5 comprising:

(a) combining components (a); (b); trialkanolamine and/or alkali metal base; alcohol solvent; and water at temperature about 80° C. to form clear liquid;

(b) pouring into mold to cool; and (c) allowing alcohol solvent to evaporate.

7. A melt cast process for making compositions of claim 3 comprising:

(a) combining components of (a); (b); trialkanolamine and/or alkali metal base; alcohol solvent; and water at temperature about 80° C. to form clear liquid;

(b) pouring into closed mold; and (c) allowing to cool.

* * * * *